(12) United States Patent
Nie et al.

(10) Patent No.: US 10,081,590 B2
(45) Date of Patent: Sep. 25, 2018

(54) DEVICE AND PROCESS FOR PRODUCING UNDECYLENIC ACID METHYL ESTER USING METHYL RICINOLEATE AS RAW MATERIAL

(71) Applicant: Zhejiang University of Technology, Hangzhou, Zhejiang Province (CN)

(72) Inventors: Yong Nie, Hangzhou (CN); Ying Duan, Hangzhou (CN); Ruchao Gong, Hangzhou (CN); Shangzhi Yu, Hangzhou (CN); Meizhen Lu, Hangzhou (CN); Jianbing Ji, Hangzhou (CN)

(73) Assignee: Zhejiang University of Technology (CN)

( * ) Notice: Subject to any disclaimer, the term of this patent is extended or adjusted under 35 U.S.C. 154(b) by 0 days.

(21) Appl. No.: 15/687,470

(22) Filed: Aug. 26, 2017

(65) Prior Publication Data
US 2017/0355657 A1  Dec. 14, 2017

Related U.S. Application Data

(62) Division of application No. 14/922,775, filed on Oct. 26, 2015, now abandoned.

(30) Foreign Application Priority Data

Oct. 27, 2014 (CN) .......................... 2014 1 0585158

(51) Int. Cl.
*C07C 67/333* (2006.01)
*B01J 19/12* (2006.01)
*B01J 8/02* (2006.01)

(52) U.S. Cl.
CPC .......... *C07C 67/333* (2013.01); *B01J 8/0285* (2013.01); *B01J 19/126* (2013.01); *B01J 2208/0053* (2013.01); *B01J 2208/00176* (2013.01); *B01J 2208/00442* (2013.01); *B01J 2219/0801* (2013.01); *B01J 2219/0869* (2013.01);
(Continued)

(58) Field of Classification Search
None
See application file for complete search history.

(56) References Cited

U.S. PATENT DOCUMENTS

2015/0191409 A1* 7/2015 Richards ................. C07C 55/20
554/167

* cited by examiner

*Primary Examiner* — Kishor Mayekar
(74) *Attorney, Agent, or Firm* — PROI Intellectual Property US

(57) ABSTRACT

A device and a process for producing undecylenic acid methyl ester using methyl ricinoleate as raw material are provided. The device comprises a feed pump, a raw material pre-heater, a microwave catalytic reactor, a microwave generator, a temperature controller and an infrared sensor, a condenser, a product tank and a discharge pump. The feed pump is connected with the raw material pre-heater, which is connected with the inlet of the microwave catalytic reactor. The outlet of the microwave catalytic reactor is connected with the condenser, which is connected to the product tank and the discharge pump. The microwave catalytic reactor is located in the microwave generator, which is connected with the temperature controller and the infrared sensor. The process is as follows: high-purity methyl ricinoleate, used as the raw material, is converted to methyl undecene and heptaldehyde by microwave-assisted pyrolysis process, followed by isolation and purification to produce methyl undecene.

4 Claims, 1 Drawing Sheet

(52) U.S. Cl.
CPC *B01J 2219/0871* (2013.01); *B01J 2219/0892* (2013.01); *B01J 2219/1215* (2013.01); *B01J 2219/1245* (2013.01)

DEVICE AND PROCESS FOR PRODUCING UNDECYLENIC ACID METHYL ESTER USING METHYL RICINOLEATE AS RAW MATERIAL

CROSS REFERENCE TO RELATED APPLICATIONS

The present application is a divisional application of U.S. Ser. No. 14/922,775 filed on Oct. 26, 2015 and claims priority to Chinese Patent Application CN201410585158.X filed on Oct. 27, 2014.

TECHNICAL FIELD

The present invention relates to the field of lipid chemical production technology, and particularly, to a device and a process for producing undecylenic acid methyl ester using methyl ricinoleate as raw material.

BACKGROUND

By means of saponification and acidification, undecylenic acid methyl ester can be obtained from undecylenic acid. Undecylenic acid has extensive applications. Particularly, after bromide and ammonolysis undecylenic acid can become aminoundecanoic acid, which can be polymerized to form tonylon-11 (PA11). PA11 has several advantages: it has a low water absorption rate, is good in oil resistance, can well withstand low temperature, and is easy processing, etc. PA11 has been widely used in automotive industry, military industry, electrical and electronic devices, sports equipment, food industry, medical devices, and so on. Undecylenic acid is used in large quantities in manufacturing flavors and fragrances. Musk T, which is made of undecylenic acid and has strong musk fragrance, is the raw material for the remixing of the three main synthetic flavors including the daily-use flavor. In addition, undecylenic acid also has a wide range of applications in medicine and surfactant.

Currently, the production methods of undecylenic acid mainly include direct pyrolysis of castor oil and pyrolysis of methyl ricinoleate. The method of direct pyrolysis of castor oil has some shortcomings such as high boiling point, high viscosity of castor oil and high pyrolysis temperature. The direct pyrolysis of castor oil in lead bath was once used in China to produce undecylenic acid, with the reaction temperature of higher than 600 degrees centigrade. Further issues with this process include serious coking and pollution, as well as low product yield. Since the 1980s, the direct catalytic cracking method has been studied; however, it still requires a temperature higher than 550 degrees centigrade and also has the issues of high cost of catalyst and low reusing rate. The method for producing undecylenic acid used by the French company ATO is to crack methyl esterified castor oil under high temperature, and method has already been industrialized. The technology of producing nylon-11 from undecylenic acid is monopolized by ATO. However, it also has the issues of high cracking temperature and easy coking, and the yield is only about 30%. In Chinese Patent CN101289383A, an electric heater tower's cracking furnace was provided to directly crack castor oil at the cracking temperature of 500~600 degrees centigrade. It needs superheated steam of 500~600 degrees centigrade, and the method has issues of high energy consumption, low productivity, low yield, and high equipment requirement.

Microwave heating is widely used in drying because of its unique advantages: the process of microwave heating does not need direct contact to heat supply, or other intermediate conversion processes. A microwave absorbing material can be directly and quickly heated through absorption of microwave. Microwave heating can save electricity by up to 30~50% compared to conventional heating methods. The process of producing undecylenic acid methyl ester by pyrolysis of methyl ricinoleate under microwave heating has not been reported before.

SUMMARY

This invention intends to overcome the deficiencies of the known techniques and provides a device and a process for producing undecylenic acid methyl ester using methyl ricinoleate as raw material. The device and the process have advantages of low energy consumption, high product yield, and less coking. After transesterification and vacuum distillation, castor oil can be converted into methyl ricinoleate of good fluidity and high purity. Using a microwave pyrolysis system, methyl ricinoleate can be quickly cracked to undecylenic acid methyl ester; then, isolation and purification processes are used to obtain high-purity undecylenic acid methyl ester.

The objective of the present invention is achieved by the following technical scheme. The device for producing undecylenic acid methyl ester using methyl ricinoleate as raw material comprises: a feed pump, a raw material pre-heater, a microwave catalytic reactor, a microwave generator, a temperature controller and an infrared sensor, a condenser, a product tank and a discharge pump. The feed pump is connected with the raw material pre-heater, which is connected with the inlet of the microwave catalytic reactor. The outlet of the microwave catalytic reactor is connected with the condenser, which is connected with the product tank and the discharge pump. The microwave catalytic reactor mentioned above is located in the microwave generator, which is connected with the temperature controller and the infrared sensor.

Preferably, the microwave catalytic reactor is designed with an inlet and an outlet. The inlet and the outlet are arranged in the upper or side portion of the reactor. In addition, the microwave catalytic reactor can be made of glass, ceramics or any other wave-transparent material that can stand high temperature.

Preferably, inside the microwave catalytic reactor is arranged a layer of microwave absorbing material. The microwave absorbing material may be silicon carbide, activated carbon, Fe/Co/Ni loaded alumina or zeolites, etc.

Preferably, the microwave catalytic reactor is arranged inside the microwave generator, and the microwave generator is connected with a feed inlet, a product outlet and a temperature measurement port. The feed inlet, product outlet and temperature measurement port are arranged on the top or the side of the microwave generator.

Preferably, the microwave generator is connected with the temperature controller, the infrared sensor and a paperless recorder.

The present invention also provides a process for producing undecylenic acid methyl ester using methyl ricinoleate as raw material, with specific steps as follows:

1. Set a cracking reaction temperature of the microwave generator and turn on the microwave generator to start a heating process;

2. Input into a device as mentioned above a methyl ricinoleate of high purity using the feed pump of the device, regulating a flow rate of the methyl ricinoleate using a flow meter and heating the methylricinoleate using the raw material pre-heater; the methyl ricinoleate of high purity may be obtained by subjecting raw methyl ricinoleate to transesterification and distillation;

3. At the set temperature and in the microwave catalytic reactor of the device, methyl ricinoleate is quickly cracked into methyl undecene and heptaldehyde gases; the methyl undecene and heptaldehyde gases are conveyed into the condenser via the outlet pipe; and forming a liquid product by condensing the methyl undecene and heptaldehyde gases using the condenser, conveying the liquid product into the product tank and pumping the liquid product into a distillation unit using the feed pump, and purifying the liquid product to obtain the undecylenic acid methyl ester.

Preferably, the temperature of the cracking reaction is between 400 and 600 degrees centigrade.

Preferably, the pyrolysis system is under atmospheric pressure or negative pressure. This may be achieved by venting the product tank or connecting it to a vacuum.

The beneficial effects of the present invention are as follows: 1. The process of microwave heating does not need direct contact to heat supply and other intermediate conversion process; microwave absorbing material can be directly and quickly heated through absorption of microwave; microwave heating can save electricity by up to 30~50% compared to conventional heating methods. The present invention uses microwave generating device and microwave absorbing catalytic material, leading to a uniform heating process which can reduce energy consumption and carbon deposition. 2. Compared to other high-temperature pyrolytic devices and processes, the present invention eliminates lead pollution, shortens reaction time, improves reaction efficiency, and increases product yield.

EXPLANATION OF THE REFERENCE SIGNS 1-1: feed pump
2: raw material pre-heater
3: microwave catalysis reactor
6-1: microwave generator
6-2: temperature controller
6-3: infrared sensor
6-4: condenser
5: product tank
1—discharge pump
Preferred Embodiments A detailed description of a preferred embodiment of this invention is presented as follows.

Figure 1:
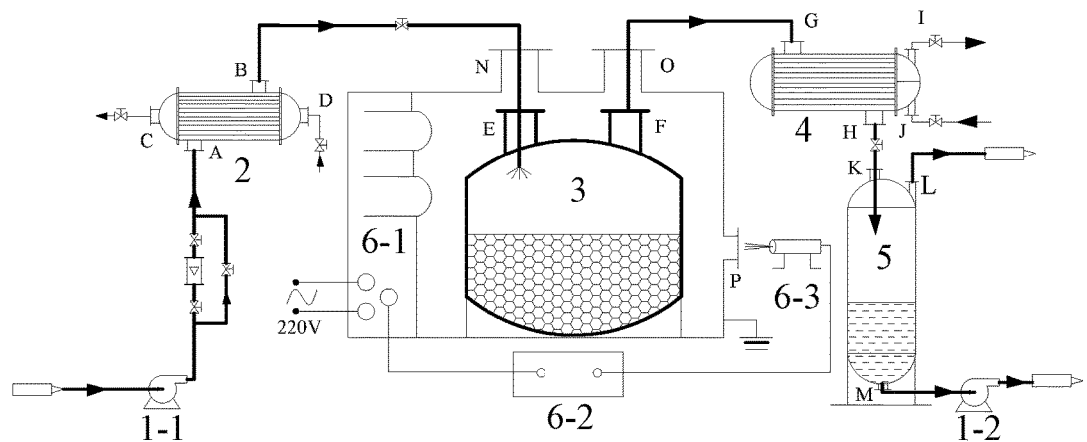
FIG. 1 shows a diagram showing a device and a process according to the present invention.
Figure 2:
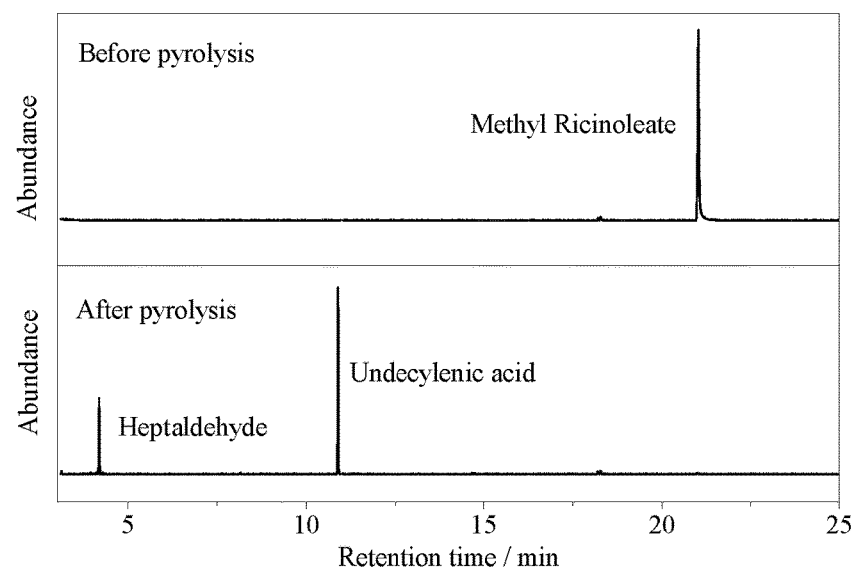
FIG. 2 presents a gas chromatography-mass spectrometer (GC-MS) total ion chromatogram of raw material and products in microwave-assisted cracking of methyl ricinoleate at high temperature.

As shown in FIG. 1, the device for producing undecylenic acid methyl ester using methyl ricinoleate as raw material comprises, among other parts, a feed pump (1-1), a raw material pre-heater (2), a microwave catalysis reactor (3), a microwave generator (6-1), a temperature controller (6-2) and an infrared sensor (6-3), a condenser (4), a product tank (5) and a discharge pump (1-2). The feed pump (1-1) is connected with the material pre-heater (2), which is connected to the inlet of the microwave catalytic reactor (3). The outlet of the microwave catalytic reactor (3) is connected with the condenser (4), which is connected to the upper port of the product tank (5). The lower port of the product tank (5) is then connected to the discharge pump (1-2). The microwave catalytic reactor (3) is placed in the microwave generator (6-1), which is connected with the temperature controller (6-2) and infrared sensor (6-3), and also a paperless recorder if necessary.

The microwave catalytic reactor (3) mentioned above has an inlet and an outlet, which are located on the top or the side of the microwave catalytic reactor (3). The microwave catalytic reactor (3) can be made of glass, ceramics or other wave-transparent material that can withstand high temperature. Inside the microwave catalytic reactor (3) is a layer of microwave absorbing material, which can be silicon carbide, activated carbon, Fe/Co/Ni loaded alumina or zeolites. The microwave catalytic reactor (3) is arranged inside the microwave generator (6-1), and the microwave generator (6-1) is connected with a feed inlet, a product outlet and a temperature measurement port. The feed inlet, the product outlet and the temperature measurement port are arranged on the top or the side of the microwave generator (6-1).

A process for producing undecylenic acid methyl ester using methyl ricinoleate as raw material comprises the specific steps as follows:

1. Set a cracking reaction temperature of the microwave generator (6-1) at 400~600 degrees centigrade and turn on the microwave generator (6-1) to start the heating process;

2. Input into a device as mentioned above a methyl ricinoleate of high purity using the feed pump (1-1), regulating a flow rate of the methyl ricinoleate using a flow meter and heating the methyl ricinoleate using the raw material pre-heater (2); the methyl ricinoleate of high purity may be obtained by subjecting raw methyl ricinoleate to transesterification and distillation;

3. At the set temperature and in the microwave catalytic reactor of the device, methyl ricinoleate is quickly cracked into methyl undecene and heptaldehyde gases; the methyl undecene and heptaldehyde gases are conveyed into the condenser (4) via the outlet pipe; and forming a liquid product by condensing the methyl undecene and heptaldehyde gases using the condenser, conveying the liquid product into the product tank (5) and pumping the liquid product into a distillation unit using the feed pump (1-2), and purifying the liquid product to obtain the undecylenic acid methyl ester.

As an embodiment of the invention: at 60 degrees centigrade, castor oil is mixed with an alkali solution of methanol to start the transesterification reaction. After 1 hour, the oil phase obtained from layering is washed with water until its pH=7. Then, rotary evaporation is performed to remove the methanol and the trace water, to obtain crude methyl ester containing 87% (by weight) of methylricinoleate. The crude methyl ester is then distilled at the reduced pressure of 100 PaA and reflux ratio of 5, during which temperature at the bottom of the distillation device is controlled at 190~210 degrees centigrade and the temperature at the top of the distillation device is controlled at about 170 degrees centigrade. The purity of the methylricinoleate obtained is higher than 99%, and the methylricinoleate obtained is used as the feedstock, or the raw material, for the subsequent microwave pyrolysis.

Silicon carbide is input to the microwave catalytic reactor (3), and the temperature of the microwave generator (6-1) is set at 500 degrees centigrade. The feed tube N is connected to the import port E of the microwave catalytic reactor (3) and the outlet tube O is connected to the export port F of the microwave catalytic reactor (3). The export F is then connected with the condenser (4), on which the ports J and I are the import and export of freezing water, respectively. The microwave generator (6-1) is turned on to make the microwave absorbing material in the microwave catalytic reactor (3) reach the set temperature and stabilize for a period of time. The raw material (high-purity methyl ricinoleate) is pumped by the feed pump (1-1), the flow rate of the raw material is measured or regulated by the flow meter, the raw material is heated by the raw material pre-heater (2), and then enters the microwave catalytic reactor via the inlet 3E thereof, and is cracked in the microwave catalytic reactor. On the raw material pre-heater, port 2A, B, C, and D are the feed port, discharge port, outlet of heat transfer oil, inlet of heat transfer oil, respectively. At the set temperature, the raw material is quickly cracked into methyl undecene and heptaldehyde gases, which flow through the outlet F into port 4G of the condenser. The methyl undecene and heptaldehyde gases are condensed in the condense to form a liquid, which flows out of the condenser through port H and enters the product tank through port K. Port L of the product tank can be vented or vacuumed or connected to a vacuum to provide a negative pressure for the pyrolysis system. The pyrolysis system may be under atmospheric pressure or negative pressure. This may be achieved by venting the product tank or connecting it to a vacuum. The liquid is pumped into a downstream distillation unit by the feed pump (1-2), and isolation and purification processes can be carried out on the liquid to obtain high-purity methyl undecene, and saponification and acidification processes may follow to finally obtain the undecylenic acid. Results of the embodiment are as follows: the liquid yield is 90.5%; the yield of the undecylenic acid is 70.2%; and selectivity of the undecylenic acid is 80.5%. By comparison, the yield is only 34~38% in the electrical heating process as reported by Chinese patent CN101289383A, and the yield in the melting lead process is only 30~32%. Compared with these processes, the yield of undecylenic acid in the present invention can be at least doubled.

It can be understood that as for technical staff in the present field, equivalent replacements or changes to the technical scheme or inventive concept in the present invention should be protected according to the claims in the present invention.

What is claimed is:

1. A process for cracking methyl ricinoleate as raw material into undecylenic acid methyl ester using a microwave pyrolysis system, the process comprising the steps as follows:
   1) setting a cracking reaction temperature at 400-600 degrees centigrade, and starting a heating process;
   2) providing methyl ricinoleate of high purity using a feed pump, regulating a flow rate of the methyl ricinoleate using a flow meter and then heating the methyl ricinoleate using a raw material pre-heater;
   3) after the heating, at the set cracking reaction temperature of 400-600 degrees centigrade and in a microwave catalytic reactor, cracking the methyl ricinoleate of high quality into methyl undecene and heptaldehyde gases, and then conveying the methyl undecene and heptaldehyde gases into a condenser via an outlet pipe; and
   4) after conveying the methyl undecene and heptaldehyde gases into the condenser via the outlet pipe, forming a liquid product by condensing the methyl undecene and heptaldehyde gases using the condenser, then conveying the liquid product into a product tank and, after conveying the liquid product into the product tank, pumping the liquid product into a distillation unit using a discharge pump, and then purifying the liquid product to obtain the undecylenic acid methyl ester.

2. The process of claim 1, further comprising the step of subjecting the raw methyl ricinoleate to transesterification and distillation to provide the methyl ricinoleate of high purity.

3. The process according to claim 1, further comprising the step of subjecting the microwave pyrolysis system under atmospheric pressure or negative pressure.

4. The process according to claim 3, further comprising a step of venting the product tank or connecting it to a vacuum so as to provide the atmospheric pressure or negative pressure under which the microwave pyrolysis system shall be subjected to.

* * * * *